(12) United States Patent
De Haan

(10) Patent No.: US 9,139,491 B2
(45) Date of Patent: Sep. 22, 2015

(54) METHANOL TO OLEFINS PROCESS

(75) Inventor: Stephen De Haan, Wayne, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 348 days.

(21) Appl. No.: 13/070,722

(22) Filed: Mar. 24, 2011

(65) Prior Publication Data

US 2012/0240615 A1    Sep. 27, 2012

(51) Int. Cl.
| | |
|---|---|
| *F25J 3/06* | (2006.01) |
| *C07C 1/20* | (2006.01) |
| *F25J 3/02* | (2006.01) |

(52) U.S. Cl.
CPC ............ *C07C 1/20* (2013.01); *F25J 3/0219* (2013.01); *F25J 3/0233* (2013.01); *F25J 3/0238* (2013.01); *F25J 3/0242* (2013.01); *F25J 2205/50* (2013.01); *F25J 2210/12* (2013.01); *F25J 2215/04* (2013.01); *F25J 2215/62* (2013.01); *F25J 2245/02* (2013.01); *F25J 2270/02* (2013.01); *F25J 2290/34* (2013.01); *F25J 2290/62* (2013.01)

(58) Field of Classification Search
USPC ............ 62/600, 617, 612, 623; 585/639, 638, 585/640, 641, 642
See application file for complete search history.

(56) References Cited

U.S. PATENT DOCUMENTS

| | | | |
|---|---|---|---|
| 3,911,041 A | 10/1975 | Kaeding et al. | |
| 4,049,573 A | 9/1977 | Kaeding | |
| 4,062,905 A | 12/1977 | Chang et al. | |
| 4,079,095 A | 3/1978 | Givens et al. | |
| 4,167,402 A | 9/1979 | Davis | |
| 4,499,327 A | 2/1985 | Kaiser | |
| 5,497,626 A * | 3/1996 | Howard et al. | 62/612 |
| 7,166,757 B2 | 1/2007 | Fung et al. | |
| 2004/0116757 A1 | 6/2004 | Van Egmond et al. | |
| 2005/0033104 A1* | 2/2005 | van Egmond et al. | 585/800 |
| 2006/0058564 A1 | 3/2006 | Sills et al. | |
| 2010/0105973 A1 | 4/2010 | De Haan et al. | |

FOREIGN PATENT DOCUMENTS

| | | |
|---|---|---|
| EP | 0060103 B1 | 4/1985 |
| EP | 0088494 B1 | 5/1985 |

OTHER PUBLICATIONS

Transmittal of International Search Report and Written Opinion issued Oct. 23, 2012 in corresponding PCT application No. PCT/US2012/029727 (10 pages).
First Office Action (with translation) issued Sep. 4, 2014 in corresponding Chinese application No. 201280021889.0 (11 pages).

\* cited by examiner

*Primary Examiner* — In Suk Bullock
*Assistant Examiner* — Sharon Pregler
(74) *Attorney, Agent, or Firm* — Osha • Liang LLP

(57) ABSTRACT

A process for chilling ethylene to required storage temperatures is disclosed, the process including: cooling an ethylene product from at least one of an ethylene production process and an ethylene recovery process via indirect heat exchange with a coolant at a temperature less than about −100° C. to decrease the temperature of the ethylene product; mixing a portion of the cooled ethylene product with methane to form the coolant; expanding at least one of the coolant, the methane, and the portion of the cooled ethylene to reduce a temperature of the coolant to less than −100° C. prior to the cooling; and feeding the heat exchanged coolant to at least one of the ethylene production process, the ethylene recovery process, and an open-loop refrigeration system.

12 Claims, 1 Drawing Sheet

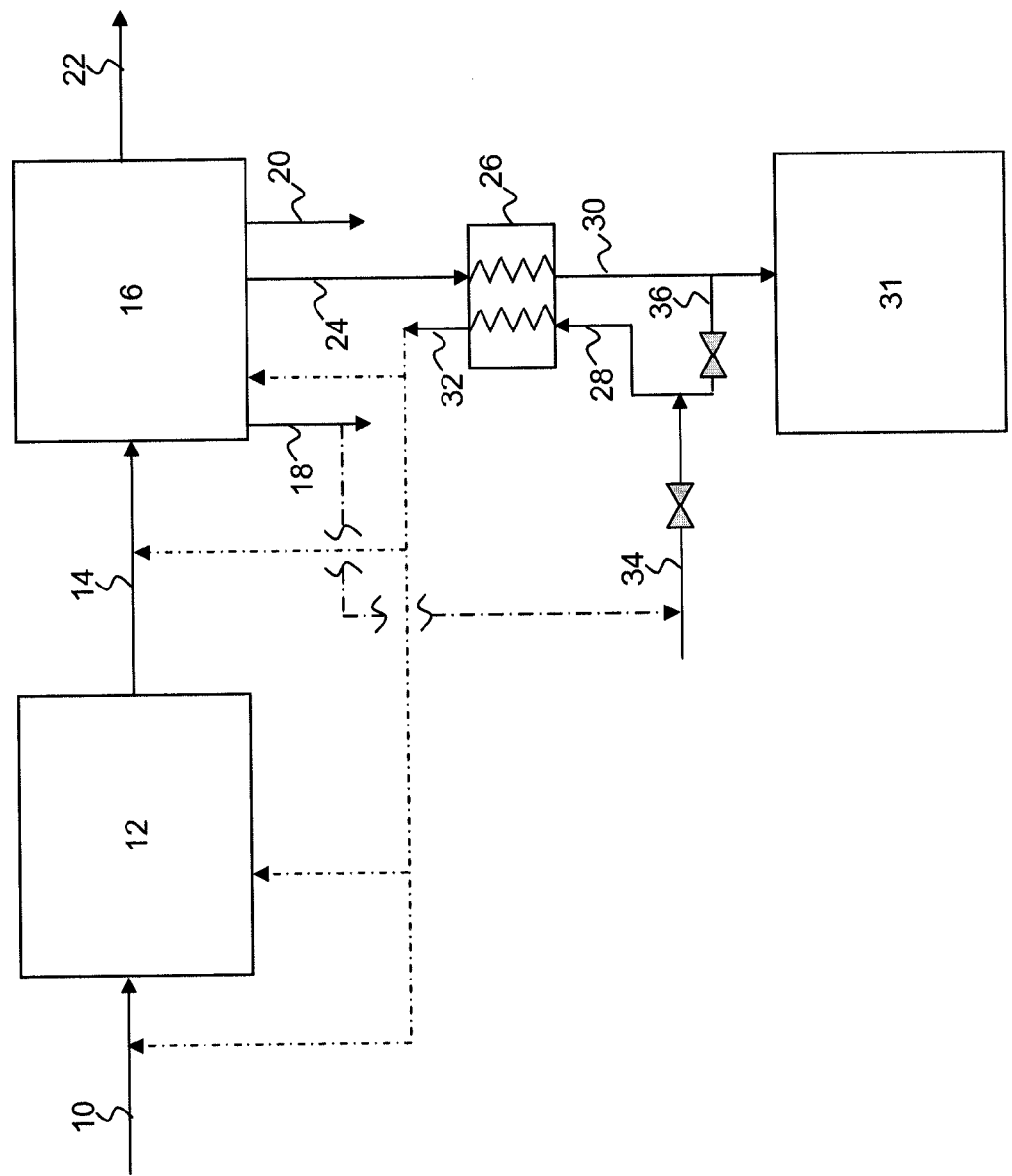

METHANOL TO OLEFINS PROCESS

BACKGROUND OF DISCLOSURE

1. Field of the Disclosure

Embodiments disclosed herein relate generally to an open-loop refrigeration system for chilling ethylene to required storage temperatures. More specifically, embodiments disclosed herein relate to an integrated process for converting methanol to olefins (MTO), where the ethylene product from the MTO process is chilled to storage temperatures using an open-loop refrigeration system.

2. Background

Limited availability and high cost petroleum sources have led to the increased cost of producing basic commodity chemicals and their derivatives from such petroleum sources. As a result, various alternative competing technologies have been developed and commercially implemented in order to produce these chemicals from non-petroleum sources at a competitive cost.

One such technology involves catalytically converting methanol to olefins (MTO). Methanol is a readily available feedstock, which can be manufactured both from petroleum as well as from non-petroleum sources, for example, by fermentation of biomass or from synthesis gas.

A typical MTO process, as disclosed in U.S. Pat. No. 4,499,327, which is hereby incorporated in its entirety, involves contacting methanol with a zeolite catalyst, such as aluminosilicate, under conditions of temperature and pressure in order to produce olefins, such as ethylene. Ethylene is an extremely valuable commodity chemical for producing various chemical derivatives and polymers used in many commercial as well as consumer products and applications.

Before ethylene produced by an MTO process can be sold or used, it is necessary to recover the ethylene component in a desirable, ethylene-rich fraction by separating it from other components and impurities. For example, depending on the feedstock composition, the reaction conditions, and the extent of side reactions, an MTO effluent can contain other light olefins, diolefins and paraffins, such as methane, ethane, and propane.

One process for the separating and recovering of ethylene from an MTO process effluent involves the use of flash stages and distillation at cryogenic temperatures, as described in U.S. Pat. Nos. 7,166,757 and 4,499,327. For example, ethylene may be recovered from methane using cryogenic boiling point separation at temperatures that may be less than −90° C. Such cryogenic processes typically use closed-loop refrigeration systems, as described in U.S. Pat. No. 4,167,402, whereby a refrigerant, such as ethylene or methane, is circulated in a loop to indirectly chill the process gas, such as the MTO effluent.

The cryogenic separation can be very expensive due to both the capital cost of the specialized vessel metallurgy and refrigeration equipment, and the operating costs, including compression and cooling for the energy-intensive chill train. Additionally, closed-loop refrigeration systems may require a large inventory of a specialized refrigerant fluid. Due to these and other concerns, some MTO processes use non-cryogenic alternative methods for separation and recovery of ethylene from an MTO effluent.

One such alternative method for separating and recovering the ethylene from an MTO effluent involves physical absorption. For example, as described in U.S. patent application Ser. No. 12/260,751, which is incorporated herein by reference, an extractive distillation process using a physical absorbent, such as a $C_2$-$C_4$ hydrocarbon, may be used to concurrently absorb ethylene from a mixture of ethylene and methane, and to separate the methane from the ethylene and the absorbent at non-cryogenic temperatures of higher than approximately −40° C.

One trade-off of using a non-cryogenic method for separating the MTO effluent to recover an ethylene-rich fraction is that the resulting ethylene-rich fraction must either be stored as a gas at a high pressure or refrigerated to allow for atmospheric storage as a cryogenic liquid. The high-pressure gas storage option may require high capital costs, including high-pressure heavy-wall spherical storage vessels, and high compression costs. In the alternative, using a closed-loop refrigeration system to subcool the ethylene-rich fraction for atmospheric storage may be expensive, including the cost of an additional refrigeration compressor. Further, the cryogenic temperatures achieved via closed-loop refrigeration may not be low enough to prevent ethylene flashing in the atmospheric storage tank and require the use of tank re-compressors.

SUMMARY OF THE DISCLOSURE

In one aspect, embodiments disclosed herein relate to a process for chilling ethylene to required storage temperatures, the process including: cooling an ethylene product from at least one of an ethylene production process and an ethylene recovery process via indirect heat exchange with a coolant at a temperature less than about −100° C. to decrease the temperature of the ethylene product; mixing a portion of the cooled ethylene product with methane to form the coolant; expanding at least one of the coolant, the methane, and the portion of the cooled ethylene to reduce a temperature of the coolant to less than −100° C. prior to the cooling; and feeding the heat exchanged coolant to at least one of the ethylene production process, the ethylene recovery process, and an open-loop refrigeration system.

In another aspect, embodiments disclosed herein relate to a process for conversion of methanol to olefins, the process including: contacting methanol with a catalyst in a methanol-to-olefins reactor system; recovering an effluent from the methanol-to-olefins reactor system comprising methane, ethane, ethylene, and $C_3^+$ hydrocarbons; separating the effluent at a temperature of greater than approximately −90° C. to recover a light fraction comprising the methane and a heavy fraction comprising the ethane, the ethylene, and the $C_3^+$ hydrocarbons; separating the heavy fraction to form an ethane-rich fraction, an ethylene-rich fraction, and one or more fractions comprising the $C_3^+$ hydrocarbons; cooling the ethylene-rich fraction via indirect heat exchange with a coolant at a temperature less than about −100° C.; mixing a portion of the cooled ethylene-rich fraction with methane to form the coolant; expanding at least one of the coolant, the methane, and the portion of the cooled ethylene to reduce a temperature of the coolant to less than −100° C. prior to the cooling; and feeding the heat exchanged coolant to at least one of the methanol-to-olefins reactor system, the separating the effluent, and an open-loop refrigeration system used in at least one of the methanol-to-olefins reactor system and the separating the effluent.

Other aspects and advantages will be apparent from the following description and the appended claims.

BRIEF DESCRIPTION OF DRAWINGS

FIG. 1 is a simplified diagram of a process for cooling ethylene to storage temperatures according to embodiments disclosed herein.

DETAILED DESCRIPTION

In one aspect, embodiments disclosed herein relate generally to an open-loop refrigeration system for chilling ethylene to required storage temperatures. The chilling of ethylene to storage temperatures may be required for any number of processes for producing ethylene, such as thermal or catalytic cracking of hydrocarbons, methanol-to-olefins (MTO) processes, and many others. In other aspects, embodiments disclosed herein relate to an integrated process for converting methanol to olefins (MTO), where the ethylene product from the MTO process is chilled to storage temperatures using an open-loop refrigeration system.

Referring now to FIG. 1, a simplified process flow diagram for chilling ethylene to storage temperatures according to embodiments disclosed herein is illustrated. A hydrocarbon feedstock is fed via flow line 10 to an ethylene production process 12 for converting at least a portion of the feedstock to ethylene. For example, ethylene production process 12 may be a catalytic cracking process, a thermal or steam cracking process, or a methanol-to-olefins process, among others. The effluent from ethylene production process 12 may be recovered via flow line 14, and the effluent may include any number of components, including one or more of water, hydrogen, carbon monoxide, carbon dioxide, methane, methanol, ethane, ethylene, propane, propylene, as well as various other $C_{3+}$ or $C_{4+}$ hydrocarbons. The effluent may then be fed via flow line 14 to ethylene product recovery zone 16, where the various components may be separated to form one or more product streams 18, 20, 22, such as, for example, a methane rich fraction, an ethane-rich fraction, and one or more $C_{3+}$ hydrocarbon fractions, respectively, and an ethylene-rich product in stream 24.

As used herein, "rich" fractions contain at least 50% by weight of the indicated component. In some embodiments, the ethylene-rich fraction may contain at least 90% ethylene; at least 95% ethylene in other embodiments; at least 98% ethylene in other embodiments; at least 99% ethylene in other embodiments; at least 99.5% ethylene in other embodiments; and at least 99.8% ethylene in yet other embodiments. The targeted concentration of the indicated component in the streams may depend upon downstream requirements; for example, where the ethylene is to be used in a polymerization process, "polymer grade" ethylene, containing greater than 99% by weight ethylene, may be required.

The ethylene-rich fraction recovered via stream 24 may be at a temperature, for example, in the range from about 0° C. to about −60° C., such as about −10° C. to about −50° C., where the temperature may depend upon the particular ethylene product recovery process 16 (i.e., the manner in which the ethylene is recovered from effluent stream 14).

Prior to sale or use of the ethylene product, the ethylene product may be temporarily held in a storage tank, such as an atmospheric storage tank. For storage of ethylene in an atmospheric storage tank, the ethylene-rich product in stream 24 is typically sub-cooled to temperatures less than −100° C., such that the ethylene may be stored as a liquid.

The ethylene-rich fraction in stream 24 may be cooled or sub-cooled to the desired storage temperature in heat exchange system 26, via indirect heat exchange with a coolant fed via flow stream 28, which is at a sufficiently low temperature, such as less than about −90° C., −95° C., −100° C., −103° C., −105° C., or −110° C. The chilled ethylene-rich fraction may be recovered from heat exchange system 26 via flow line 30 and fed to storage tank 31. The warmed coolant may be recovered from heat exchange system 26 via flow line 32.

The coolant provided via flow stream 28 may be formed by mixing methane, fed via flow line 34, with a portion 36 of the cooled ethylene-rich fraction recovered via flow line 30. The low coolant temperature may be provided by flashing (expanding) the methane, ethylene, or a mixture thereof, prior to feeding the coolant to heat exchange system 26.

The heat exchanged coolant recovered via flow line 32, or a portion thereof, may then be fed to at least one of the ethylene production process 12, the ethylene recovery process 16, may be used to cool one or more product or feed streams, such as feed 10, effluent 14, $C_{3+}$ hydrocarbon fraction 22, ethane-rich fraction 20, or may be used in an open-loop refrigeration system or heating system that may form part of the ethylene production process 12 or the ethylene recovery process 16.

In some embodiments, such as where a methane-rich fraction is recovered from separation zone 16, a portion of the methane-rich fraction recovered via flow line 18 may be used as the methane portion of the coolant, such as fed via flow line 34.

As mentioned above, ethylene production process 12 may include any number of processes, including catalytic cracking, thermal or steam cracking, and methanol-to-olefins processes, among others. Hydrocarbon feedstocks useful in ethylene production processes according to embodiments disclosed herein may include one or more of methane, ethane, as well as linear, branched, cyclic, etc. C3 olefins and paraffins, C4 olefins and paraffins, C5 olefins and paraffins, and C6+ olefins, paraffins, and aromatics.

Ethylene production processes useful in embodiments disclosed herein may convert various oxygenates to olefins. Other hydrocarbon feedstocks that may be useful include ethanol and other alcohols as may be formed from petroleum sources and non-petroleum sources, including alcohols produced by fermentation or synthesis gas. In particular, processes disclosed herein may be used to convert methanol to olefins, and to separate and recover ethylene from a methanol-to-olefins reaction effluent. For example, a feedstock containing one or more oxygenated compounds may be converted to one or more olefins. Non-limiting examples of suitable oxygenate compounds include alcohols, including straight and branched chain aliphatic alcohols and their unsaturated counterparts, such as methanol, ethanol, n-propanol and isopropanol; alkyl ethers such as dimethyl ether, diethyl ether, methyl ethyl ether and di-isopropyl ether; alkyl ketones such as dimethyl ketone; aldehydes such as formaldehydes, dimethylcarbonate and various acids such as acetic acid. In some embodiments, the oxygenate feedstock may include methanol as the primary oxygenate compound. In other embodiments, the oxygenated feedstock may consist essentially of methanol.

In some embodiments, the ethylene production process is a methanol-to-olefins process (MTO). A methanol-to-olefins (MTO) process requires separating the effluent in order to recover an ethylene-rich fraction from other compounds and impurities, including: light olefins; diolefins; and paraffins, such as methane, ethane, and propane. In some embodiments, the separation of ethylene and methane can be accomplished via cryogenic flash distillation, wherein the cryogenic cooling may be provided via a closed-loop refrigeration system. In other embodiments, a non-cryogenic extractive distillation using an absorbent may be used to separate the ethylene from the methane in the MTO effluent.

MTO processes using non-cryogenic methods for separating and recovering an ethylene-rich fraction from an MTO effluent, such as extractive distillation, are not capable of achieving temperatures low enough to liquefy and sub-cool the ethylene-rich fraction for atmospheric storage. Adding a closed-loop refrigeration system to such an MTO process for sub-cooling the ethylene-rich fraction requires substantial capital and operating expense, including an additional compressor and refrigeration loop. An open-loop refrigeration system using a portion of the ethylene-rich fraction of the MTO effluent as a mixed refrigerant according to embodiments disclosed herein may be used to sub-cool the ethylene-rich fraction in order to allow atmospheric storage, as described above. In some embodiments, an existing MTO process may be retrofitted with open-loop refrigeration system using minimal additional equipment and, in contrast to closed-loop refrigeration, avoiding the need for an additional refrigeration compressor. Additionally, as compared to cryogenic cooling systems for recovering ethylene, sub-cooling ethylene according to embodiments disclosed herein may eliminate flashing when the ethylene enters the storage tank, which may allow for use of smaller tank re-compressors.

A variety of embodiments for the MTO reaction system may be used. In some embodiments, the MTO reactor system may include a single reaction zone. In other embodiments, the MTO reactor system may comprise multiple reaction zones arranged in series and/or parallel. In some embodiments, the methanol may travel upflow through the one or more reaction zones. In other embodiments, the methanol may travel downflow through the one or more reaction zones.

One or a combination of a variety of reactor types can be used in the MTO reactor system, including, but not limited to: fixed bed reactors; dense, bubbling, riser-type, or slurry-type fluidized bed reactors; boiling point reactors; and catalytic distillation reactor systems, for example, as described in U.S. Pat. Nos. 4,076,796 and 6,287,522. One of ordinary skill in the art would recognize that other types of reactors may also be used.

The catalyst used in the MTO reactor system may be one of a homogeneous catalyst or a heterogeneous catalyst. In some embodiments, the catalyst may be a zeolite or molecular sieve catalyst. In one specific embodiment, the catalyst may be a crystalline aluminosilicate zeolite catalyst, such as those disclosed in U.S. Pat. Nos. 4,062,905, 4,079,095, 3,911,041, and 4,049,573. One of ordinary skill in the art would recognize that other types of catalysts can also be used.

The MTO reaction process can be conducted over a wide range of temperatures, such as in the range from approximately 200° C. to approximately 1000° C. In some embodiments, the temperature of the MTO reaction system may be between approximately 200° C. and approximately 700° C. In other embodiments, the temperature of the MTO reaction system may be between approximately 300° C. and approximately 600° C. In yet other embodiments, the temperature of the MTO reaction system may be between approximately 350° C. and approximately 550° C.

Similarly, the process can be conducted over a wide range of pressures including autogenous pressure. Typical partial pressures of the feedstock, exclusive of any diluent therein employed in the process, is in the range from approximately 0.1 kPaa to approximately 5 MPaa. In some embodiments, the pressure of the MTO reaction system may be between approximately 5 kPaa and approximately 1 MPaa. In other embodiments, the pressure of the MTO reaction system may be between approximately 20 kPaa and approximately 500 kPaa.

The olefins produced by an MTO process according to embodiments disclosed herein may include one or more of $C_2$ to $C_{30}$ olefins and/or diolefins. In some embodiments, the olefins produced may include one or more of $C_2$ to $C_8$ olefins. In other embodiments, the olefins produced may include one or more of $C_2$ to $C_6$ olefins. In yet other embodiments, the olefins produced may include one or more of $C_2$ to $C_4$ olefins, for example, ethylene and propylene. In still other embodiments, the olefins produced may consist essentially of ethylene.

In some embodiments, the concentration of ethylene in the MTO reactor effluent may be at least approximately 5 mole percent. In other embodiments, the concentration of ethylene in the MTO reactor effluent may be at least approximately 10 mole percent. In yet other embodiments, the concentration of ethylene in the MTO reactor effluent may be at least approximately 20 mole percent. In still other embodiments, the concentration of ethylene in the MTO reactor effluent may be at least approximately 30 mole percent.

An MTO reaction may also produce non-olefin products, including but not limited to, paraffins, acetylenes, ethers, and esters. For example, an MTO reaction effluent may include methane, ethane, propane, n-butane, isobutane, n-butene, isobutene, butadiene, dimethyl ether and water. The presence and concentrations of these by-products may vary depending, for example, on the feedstock qualify, the type and size of reactor, the reaction conditions, and the type and condition of the catalyst used, among others.

In some embodiments, the concentration of methane in the MTO reactor effluent may be less than approximately 30 mole percent. In other embodiments, the concentration of methane in the MTO reactor effluent may be less than approximately 20 mole percent. In yet other embodiments, the concentration of methane in the MTO reactor effluent may be less than approximately 10 mole percent. In still other embodiments, the concentration of methane in the MTO reactor effluent may be less than approximately 5 mole percent. In other embodiments, the concentration of methane in the MTO reactor effluent may be less than approximately 2 mole percent.

In order to recover ethylene of sufficient purity, the MTO reactor effluent may undergo one or more separation stages. For example, it may be desired or necessary to separate ethylene from various reactants and products, including but not limited to, ethers and alcohols, carbon dioxide, water, methane, and other reactants, reaction products, and diluents.

In some embodiment, at least a portion of the MTO reactor effluent may be fed to an extraction system for removing any methanol and/or ethers contained therein using an aqueous solvent, such as water or glycol. An aqueous fraction having an increased concentration of methanol and ethers may be recovered from the extraction system. A hydrocarbon phase including methane and ethylene, and lean in methanol and ethers, may be recovered from the reactor effluent in the extraction system. The hydrocarbon phase may then be sent for further component separation(s). In some embodiments, the MTO reactor effluent may be compressed prior to any further separation(s).

Carbon dioxide that may be present in the MTO reactor effluent may also require removal. For example, an olefin product specification may require removal of carbon dioxide from the MTO reactor effluent. Further, exposure of the carbon dioxide containing stream to below-sublimation temperatures may result in equipment damage and frozen piping. Methods commonly known and used in the industry, such as caustic solution treatment or amine absorption, may be used to remove $CO_2$ from the MTO reactor effluent. In some embodiments, the reactor effluent may be contacted with a caustic solution to separate at least a portion of the carbon dioxide present in the reactor effluent. If necessary, the reactor effluent may be compressed prior to the carbon dioxide removal stage.

The presence of water in the MTO reaction effluent can lead to a number of problems. For example, cooling and/or compressing the reaction effluent may result in formation of water condensate that can damage equipment and freeze pipes. Therefore, dehydration of the reactor effluent to remove water using one of a number of techniques commonly used in the industry may be required or may be optionally performed based on process schemes and temperatures employed. In some embodiments, a molecular sieve dryer may be used for separating at least a portion of the water, drying the reactor effluent. In other embodiments, a chemical desiccant such as glycol may be used for drying the reactor effluent. In yet other embodiments, a portion of the water in the reactor effluent may be condensed and the remaining effluent may be dried. Other dehydration techniques commonly known and used in the industry may also be used. If necessary, the reactor effluent may be compressed prior to the water removal stage.

Most hydrocarbon byproducts and impurities may be separated from the ethylene in the MTO effluent via fractional distillation at non-cryogenic temperatures. For example, a de-propanizer may be used to separate $C_3$ and heavier materials, and a de-ethanizer may be used to separate ethane and heavier materials from ethylene and lighter materials. In some embodiments, the temperatures for such non-cryogenic separations may be higher than approximately $-90°$ C. In other embodiments, the temperatures may be higher than approximately $-60°$ C. In yet other embodiments, the temperatures may be higher than approximately $-40°$ C.

A particularly challenging separation is that of ethylene from methane and other lights (hydrogen, nitrogen, etc.) that may be contained within the MTO reactor effluent due to their low boiling points. Separating these components using fractional distillation would potentially require cryogenic temperatures lower than approximately $-100°$ C. For example, such temperatures may be achieved via a closed-loop refrigeration system using a specialized refrigerant fluid, an additional refrigeration compressor, and a refrigeration loop.

Non-cryogenic separation method alternatives according to embodiments disclosed herein may be used to separate the ethylene from the methane and the lights within the MTO effluent. For example, extractive distillation using an absorbent, such as a $C_2$-$C_4$ hydrocarbon absorbent, may be used to separate and recover ethylene and higher olefinic hydrocarbons from an MTO reaction effluent at non-cryogenic temperatures. An MTO reaction effluent, including ethylene and methane, can be contacted with a hydrocarbon absorbent in an extraction distillation system, whereby at least a portion of the ethylene may be absorbed by the hydrocarbon absorbent. The methane and lighter materials may be recovered as an overheads fraction, and the ethylene and the $C_2$-$C_4$ hydrocarbon absorbent may be recovered as a bottoms fraction. A person of ordinary skill in the art would recognize that other non-cryogenic separation methods of ethylene from the MTO effluent can also be used.

In some embodiments, the hydrocarbon absorbent may be a $C_2$ to $C_4$ hydrocarbon, for example, including at least one of ethane, propane, propylene, n-butane, isobutane, n-butene, and isobutene. In other embodiments, the hydrocarbon absorbent may consist essentially of propane.

In some embodiments, the extraction distillation system may include one or more extractive distillation and/or distillation stages. For example, the MTO reactor effluent may be contacted with the hydrocarbon absorbent in one or more extractive distillation and/or distillation stages arranged in series within a single column or in a series of multiple columns.

The one or more extractive distillation and/or distillation stages may comprise trays and/or packing for providing a sufficient surface for the contacting. In some embodiments, the methanol-to-olefins reactor effluent and hydrocarbon absorbent may be contacted counter-currently in the extractive distillation system. In other embodiments, the methanol-to-olefins reactor effluent and hydrocarbon absorbent may be contacted co-currently in the extractive distillation system.

In some embodiments, the extractive distillation system may be operated at an overheads temperature of $-90°$ C. or higher; at an overheads temperature of $-50°$ C. or higher in other embodiments; at an overheads temperature of $-40°$ C. or higher in other embodiments; at an overheads temperature of $-20°$ C. or higher in other embodiments; at an overheads temperature of $-10°$ C. or higher in other embodiments; and at an overheads temperature of $0°$ C. or higher in yet other embodiments.

In general, the pressure of the overhead fraction recovered from the extractive distillation system may be maintained at a level required for the distillation and as required for absorption of ethylene into the hydrocarbon absorbent. In some embodiments, the overheads pressure may be in the range from about 0.01 MPag to 10 MPag; in the range from about 0.1 MPag to 4 MPag in other embodiments; in the range from about 0.5 MPag to 3 MPag in other embodiments; and in the range from approximately 0.5 MPag to 1 MPag in yet other embodiments.

In some embodiments, at least 70 percent of the ethylene in the MTO effluent may be absorbed and recovered from the extractive distillation system as a bottoms fraction along with the hydrocarbon absorbent; at least 80 percent of the ethylene may be absorbed and recovered in other embodiments; and at least 90 percent of the ethylene may be absorbed and recovered in yet other embodiments.

The bottoms fraction may be further separated to recover an ethylene-rich fraction from the hydrocarbon absorbent, such as a $C_2$-$C_4$ hydrocarbon absorbent. For example, the ethylene-rich fraction may be separated from the $C_2$-$C_4$ hydrocarbon absorbent using fractional distillation. The concentration of ethylene in the ethylene-rich fraction may vary, depending upon the desired end use, as noted above.

The ethylene-rich fraction recovered from the MTO effluent using non-cryogenic separation methods, for example, extractive distillation, may be further sub-cooled using open-loop refrigeration according to embodiments disclosed herein. In contrast to closed-loop refrigeration, where a separate refrigerant fluid is circulated in a refrigeration loop in order to accomplish the sub-cooling of the ethylene-rich fraction, open-loop refrigeration according to embodiments disclosed herein may use a portion of the sub-cooled ethylene-rich fraction as the refrigerant.

For example, at least a portion of the ethylene-rich fraction may be fed to a condensing zone of one or more heat exchangers, wherein the ethylene-rich fraction may be sub-cooled via indirect heat exchange with a refrigerant.

In some embodiments, the heat exchanger may be a brazed aluminum heat exchanger, commonly referred to as a "cold box". In other embodiments, the heat exchanger may be a shell-and-tube heat exchanger having specialized metallurgy suitable for cryogenic operating temperatures. A person of ordinary skill in the art would understand that other types of heat exchangers can also be used.

The sub-cooled ethylene-rich fraction may be recovered from the condensing zone of the heat exchanger at a low enough temperature to allow storage at atmospheric conditions, without causing excessive ethylene flashing. In some embodiments, the temperature of the sub-cooled ethylene-rich fraction may be less than about −100° C.; less than −103° C. in other embodiments; less than −105° C. in other embodiments; and less than −110° C., −120° C., or −130° C. in yet other embodiments.

As noted above, a portion of the sub-cooled ethylene may be mixed with methane to form the coolant (mixed refrigerant) used to sub-cool the ethylene. The ethylene, methane, or mixed refrigerant may be expanded to achieve temperatures suitable to sub-cool the ethylene to temperatures as noted above. In some embodiments, the temperature of the expanded mixed refrigerant may be less than −102° C.; less than −105° C. in other embodiments; and less than −110° C., −120° C., or −130° C. in yet other embodiments.

The chilled mixed refrigerant may then be fed to a cooling zone of the one or more heat exchangers in order to sub-cool the ethylene-rich fraction via indirect heat exchange. The mixed refrigerant recovered from the cooling zone of the one or more heat exchangers may then be fed to the MTO process, the MTO effluent separation system, or a refrigeration system used in either.

As described above, embodiments disclosed herein provide for the cooling or sub-cooling of ethylene product streams to storage temperatures, where the refrigerant used for the cooling is provided by an open-loop system using the ethylene product and methane as a mixed refrigerant. Advantageously, processes according to embodiments disclosed herein provide for a robust and simple way to sub-cool an ethylene-rich fraction produced in a number of chemical processes, including MTO processes. In contrast to closed-loop refrigeration systems, using open-loop refrigeration according to embodiments disclosed herein does not require a separate refrigeration fluid, and may therefore allow for re-using a lot of the existing piping and equipment, including the existing compressor.

Another advantage of processes according to embodiments disclosed herein is the reduced capital equipment and operating costs. For example, using open-loop refrigeration according to embodiments disclosed herein may eliminate the cost of an additional refrigeration compressor and/or the separate refrigeration loop, or may allow for use of a smaller tank re-compression system.

Yet another advantage of processes according to embodiments disclosed herein is the ability to achieve refrigeration temperatures using mixed refrigeration lower than those achievable using single-component refrigeration. For example, injecting methane into the subcooled ethylene-rich fraction prior to flashing may reduce the vaporization temperature, and, therefore, may lower the resulting mixed refrigerant temperatures available for the subcooling.

Still another advantage of processes according to embodiments disclosed herein is the potentially reduced flashing of the ethylene-rich fraction sent to atmospheric storage. For example, closed-loop refrigeration may not be capable of reducing the temperature of the ethylene-rich fraction to lower than approximately −102° C. prior to sending the ethylene-rich fraction to atmospheric storage, where the ethylene may flash when fed to the storage tank. In contrast, using open-loop refrigeration according to embodiments disclosed herein may allow sub-cooling of the ethylene-rich fraction to temperatures below −102° C. in order to minimize the flashing during transport to atmospheric storage.

Yet another advantage of processes according to embodiments disclosed herein is the ability to effectively and cost-efficiently retrofit an existing MTO process in order to sub-cool the ethylene-rich fraction recovered from the MTO effluent. For example, an existing MTO process may use non-cryogenic processes, such as extractive distillation using a physical absorbent, for separating ethylene from methane in the MTO effluent. Adding a new closed-loop refrigeration system just for sub-cooling the ethylene-rich effluent may be cost-prohibitive, as discussed above. In contrast, using an open-loop refrigeration system to retrofit an existing MTO process that uses non-cryogenic separation processes may allow for an effective and cost-efficient method to sub-cool the ethylene-rich fraction of the MTO effluent.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for chilling ethylene to required storage temperatures, the process comprising:
    cooling an ethylene product comprising greater than 90 wt % ethylene via indirect heat exchange with a coolant to decrease the temperature of the ethylene product to a temperature of less than −100° C., the ethylene product from at least one of an ethylene production process and an ethylene recovery process;
    mixing a portion of the cooled ethylene product with methane to form the coolant;
    expanding at least one of the coolant, the methane, and the portion of the cooled ethylene product to reduce a temperature of the coolant to less than −100° C. prior to the cooling; and
    feeding the heat exchanged coolant to at least one of the ethylene production process, the ethylene recovery process, and an open-loop refrigeration system.

2. The process of claim 1, wherein the ethylene product is at a temperature in the range from about −10° C. to about −50° C.

3. The process of claim 1, further comprising feeding the cooled ethylene product to an atmospheric storage tank.

4. The process of claim 1, wherein the ethylene production process is a methanol-to-olefins process or wherein the ethylene recovery process comprises an ethylene recovery system for recovery of ethylene produced in a methanol-to-olefins process.

5. A process for conversion of methanol to olefins, the process comprising:
    contacting methanol with a catalyst in a methanol-to-olefins reactor system;
    recovering an effluent from the methanol-to-olefins reactor system comprising methane, ethane, ethylene, and $C_3^+$ hydrocarbons;
    separating the effluent at a temperature of greater than approximately −90° C. to recover a light fraction comprising the methane and a heavy fraction comprising the ethane, the ethylene, and the $C_3^+$ hydrocarbons;
    separating the heavy fraction to form an ethane-rich fraction, an ethylene-rich fraction comprising greater than 90 wt % ethylene, and one or more fractions comprising the $C_3^+$ hydrocarbons;
    cooling the ethylene-rich fraction to a temperature of less than −100° C. via indirect heat exchange with a coolant;
    mixing a portion of the cooled ethylene-rich fraction with methane to form the coolant;
    expanding at least one of the coolant, the methane, and the portion of the cooled ethylene to reduce a temperature of the coolant to less than −100° C. prior to the cooling; and feeding the heat exchanged coolant to at least one of the methanol-to-olefins reactor system, the separating the effluent, and an open-loop refrigeration system used in at least one of the methanol-to-olefins reactor system and the separating the effluent.

6. The process of claim 5, wherein the ethylene-rich fraction is at a temperature in the range from about −10° C. to about −50° C.

7. The process of claim 5, further comprising feeding the cooled ethylene-rich fraction to an atmospheric storage tank.

8. The process of claim 7, wherein the ethylene-rich fraction comprises at least 98% by weight ethylene.

9. The process of claim 5, further comprising contacting the heat exchanged coolant in indirect heat exchange with at least one of a refrigerant, at least one of the one or more fractions comprising the $C_3^+$ hydrocarbons, and the effluent.

10. The process of claim 5, wherein the separating the heavy fraction comprises:
fractionating the heavy fraction in one or more distillation units to separate the ethylene from the ethane and the $C_3^+$ hydrocarbons;
recovering the ethylene-rich fraction from the one or more distillation units.

11. The process of claim 5, wherein at least a portion of the light fraction is used as the methane portion of the coolant.

12. The process of claim 5, wherein the separating the effluent comprises:
contacting at least one of the effluent and the heavy fraction with an absorbent in an extractive distillation unit to partition the ethylene into the adsorbent; and
separating the ethylene from the absorbent.

* * * * *